United States Patent [19]

Tronzo

[11] Patent Number: 4,681,589
[45] Date of Patent: Jul. 21, 1987

[54] ADJUSTABLE ACETABULAR CUP PROSTHESIS AS PART OF A TOTAL CUP REPLACEMENT SYSTEM

[76] Inventor: Raymond G. Tronzo, 255 Clarke Ave., Palm Beach, Fla. 33480

[21] Appl. No.: 616,100

[22] Filed: Jun. 1, 1984

[51] Int. Cl.⁴ ............................................. A61F 2/34
[52] U.S. Cl. ...................................................... 623/22
[58] Field of Search .................... 3/1.9, 1.91, 1.911, 3/1.912, 1.913; 128/92 C, 92 CA; 623/16–23

[56] References Cited

U.S. PATENT DOCUMENTS

| | | | |
|---|---|---|---|
| 3,641,590 | 2/1972 | Michele | 3/1.912 |
| 3,840,904 | 10/1974 | Tronzo | 3/1.912 |

FOREIGN PATENT DOCUMENTS

| | | | |
|---|---|---|---|
| 2411617 | 4/1975 | Fed. Rep. of Germany | 3/1.912 |
| 2950536 | 7/1981 | Fed. Rep. of Germany | 3/1.912 |
| 3129174 | 2/1983 | Fed. Rep. of Germany | 3/1.912 |

Primary Examiner—Richard J. Apley
Assistant Examiner—David J. Isabella
Attorney, Agent, or Firm—Eugene Chovanes

[57] ABSTRACT

A total hip joint prosthesis including an acetabular cup implant of a construction permitting an initial adjustable disposition for optimum articulation with a prosthetic femoral ball mounted on a femoral prosthesis within a usual cup implant, the implant is of a trapezoidal or truncated cone shape, and external fins and a porous surface are provided to facilitate an initial and long-term positional fixation in the user, and to compensate for physiological bone changes over an extended period of time. The porous surface is preferred but an option is to use a plain surface implant used as a "press-fitted" device.

5 Claims, 10 Drawing Figures

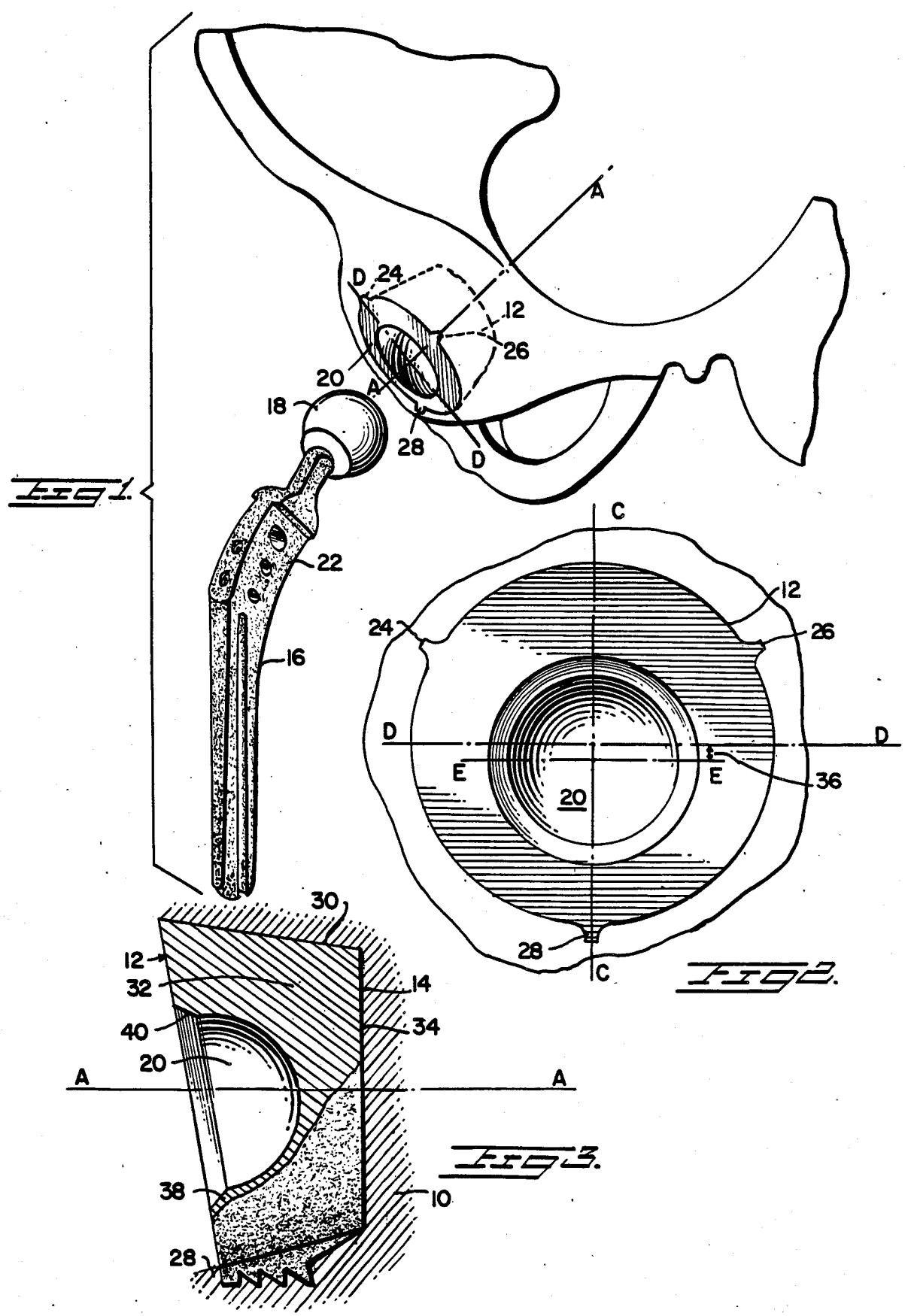

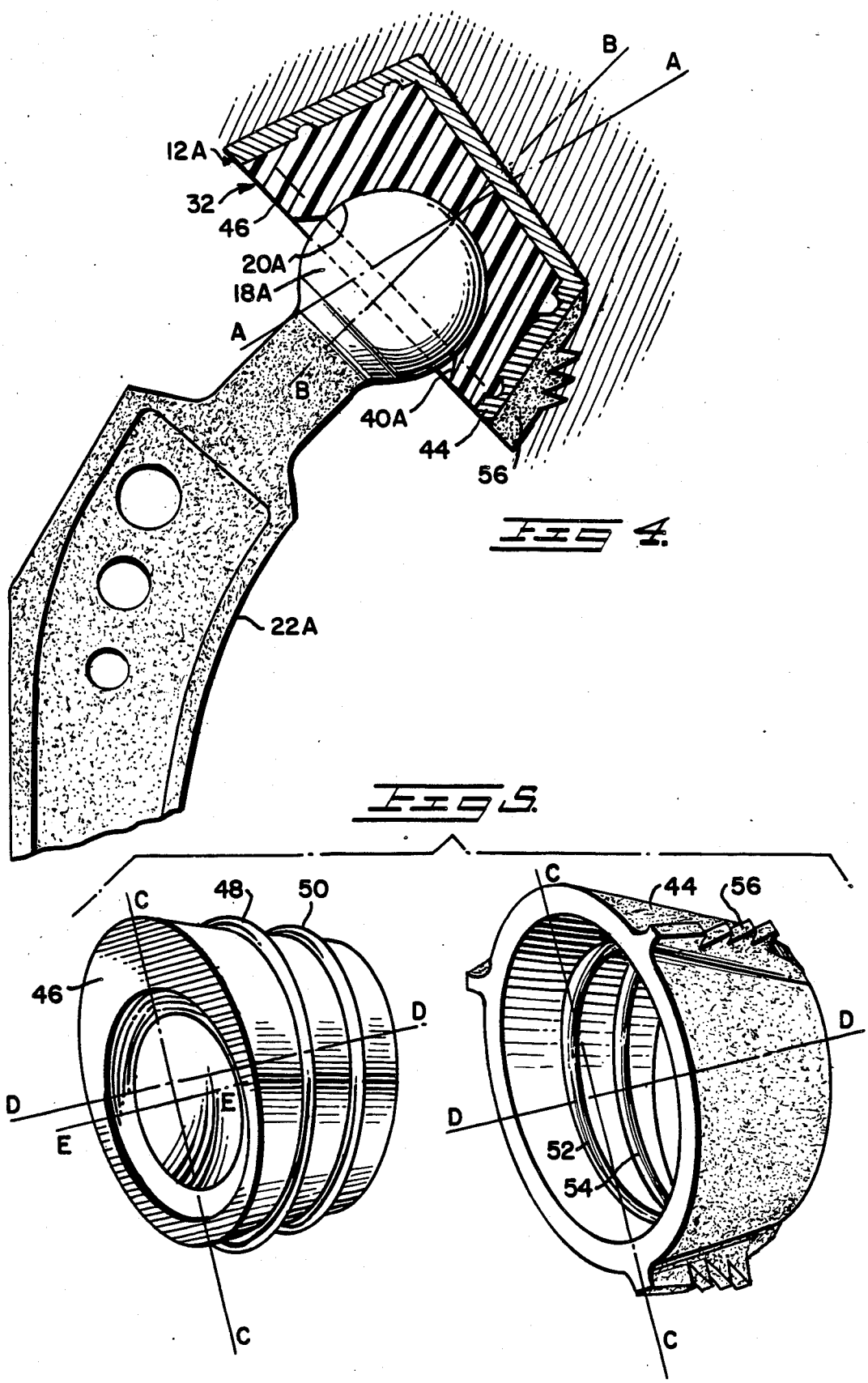

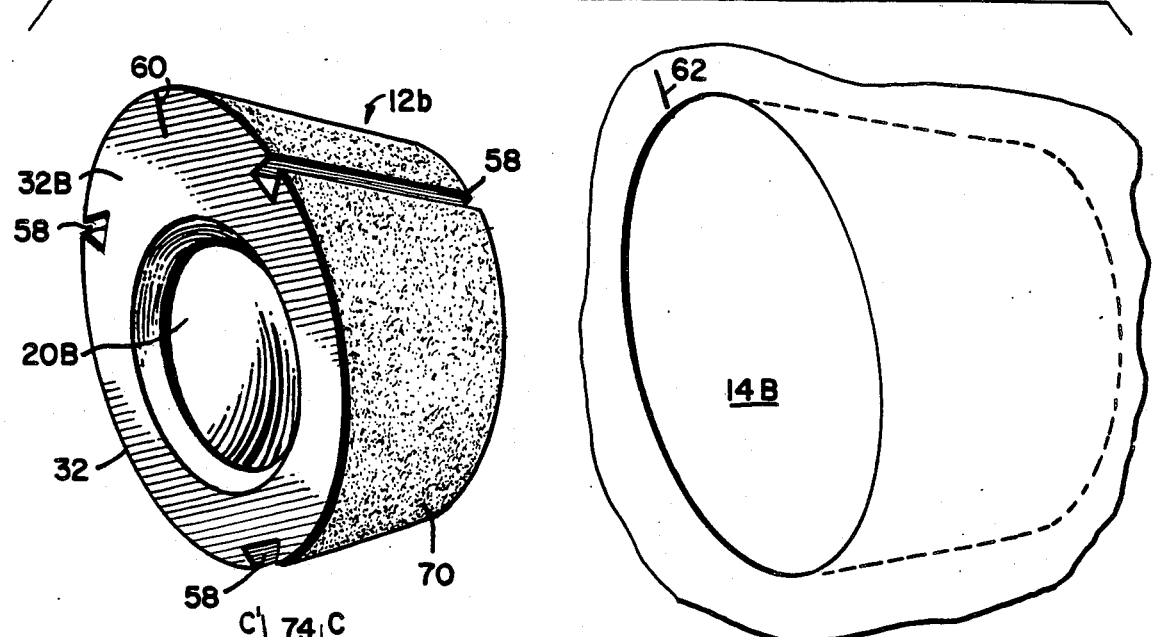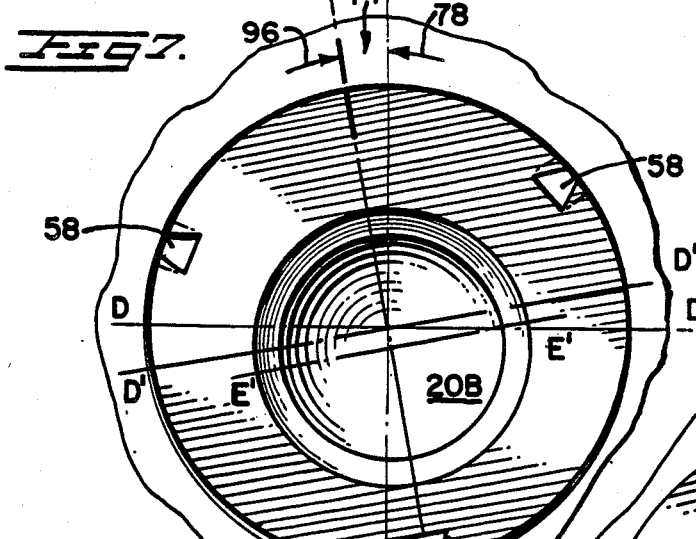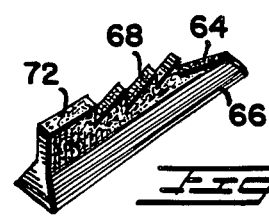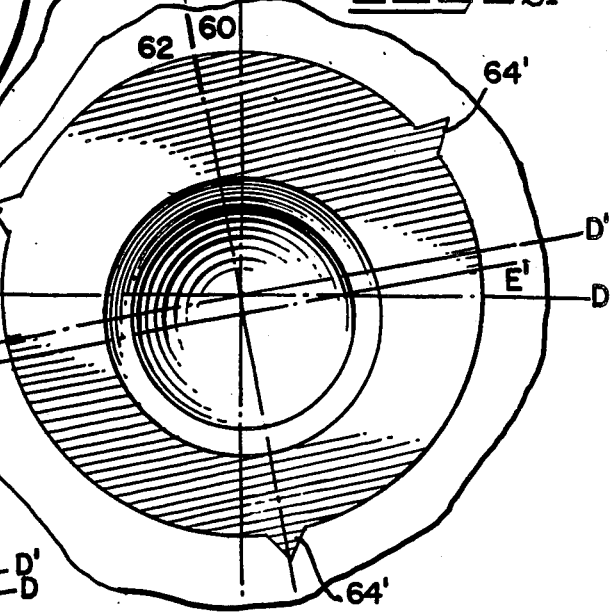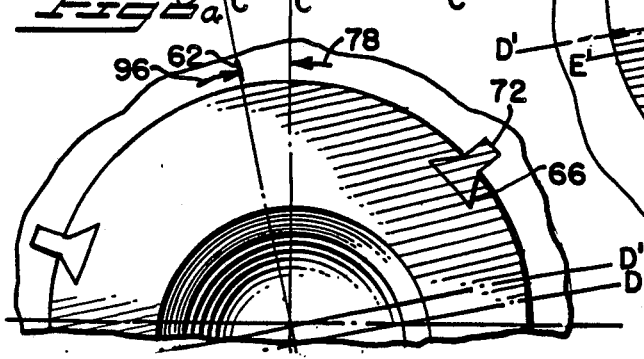

ADJUSTABLE ACETABULAR CUP PROSTHESIS AS PART OF A TOTAL CUP REPLACEMENT SYSTEM

FIELD OF THE INVENTION

The present invention relates to total hip joint prosthesis of a type including an acetabular cup implant adapted for insertion in an acetabular bone and which has a femoral ball on a femoral pin, the ball being positionally mounted within a usual ball socket in a cup implant.

Such constructions are well known in the art and exemplary of such constructions as those disclosed in my prior U.S. Pat. Nos. 3,840,904 of Oct. 15, 1974, and 3,808,606 of May 7, 1974.

The disclosures in my prior patents are incorporated herein by reference thereto for purposes of delineating an art area within which the present invention is usable. Other constructions and devices are also existing in the prior art and it is a primary purpose of the present invention to provide a new and improved design or concept for such a hip prosthesis and preferably of a total hip prosthesis.

The present invention includes features which provide for an initial positional fixation in the hip bone of a user which will facilitate optimum interaction of a femoral ball within an articulating socket in the acetabular implant, both initially and over an extended period of use by the user.

Other meritorious features will appear hereinafter in descriptions of preferred embodiments of the invention.

BACKGROUND OF THE INVENTION

Total hip joint prosthesis of a type including an acetabular cup implant provided with a ball socket for mounting operationally a femoral ball on a femoral pin are known in the art.

Some problems have existed in the prior art devices for various reasons.

It is sometimes difficult to obtain an initial and lasting relative positionment of the socket in the implant so that the ball will continue optimally functional in use regardless of positional movement or rotation of a user's leg.

The acetabular cup implant of the present invention, and as also shown in my prior U.S. patents and in devices of others in the art, have included position maintaining means such as spikes or blades or hemispheroidal devices designed to hold the implant firmly in place while resisting rotational, compressive, and distracting forces on the implant during an initial phase of bony ingrowth and subsequent fixation with respect to the bone opening in which placed. Means to relatively fix the components over a long time have additionally included use of a porous surface or coated cup design to facilitate a normal growth of bone into fixation in and with respect to the openings in the porous surface.

In combination, the heretofore used spikes or other fixation means and the porous surface have provided relatively favorable results in use.

Certain drawbacks have existed, however, in prior known devices both as regards the initial positionment of the cup within which the femoral head is rotatably mounted or contained, and initial and lengthy fixation of the acetabular cup with respect to the bone within which implanted devices have not been entirely satisfactory. As pointed out above, certain steps have heretofore been utilized to provide a friction fixation for a primary initial fixation and a secondary or continuing arrangement or means wherein the specific outer porous surfaces of the cup intergrows with the bone for a long-range fixation. This broad combination of concepts is known in the art. The present invention, however, provides new and highly improved results in construction and use of the hip prosthesis as distinguished from the prior art and the results obtained provide a most desirable initial and continuing living connection or interconnection between the implant and the bone which is independent of any sizing of the porous oversurface.

It will also be noted that the present invention is usable in such a manner that the acetabular cup with the ball socket can be positionally moved subsequent to the initial positionment in a bore provided in the bone so that the implanting position can insure optimum alignment with the femoral ball or head on a femoral pin regardless of position or use of a leg of the user and will prevent a disconnection (or dislocation) between these two portions of a prosthesis.

Also as will be apparent from the following disclosure, the so-adjustable cup implant can be provided with fins which can either be permanent or which can be placeable with respect to the implant following positionment thereof, these fins being longitudinally positioned with respect to the axis of the implant. The total external surface of the implant and/or the longitudinal fixation fins can have a porous or pore arrangement which will provide the desirable initial and continuing living connection between the implant and the bone. It can also be left bare of any porosity and left to remain fitted into its final position by a friction-fit alone, although the bony ingrowth mode of fixation will be the preferred one.

While certain forms of the present invention will be specifically shown and described hereinafter, obviously the invention is not limited to the specific structures and variations disclosed but will permit of obvious variations within the scope of the invention as defined by the claims herein.

Other and additional meritorious features and advances in the art will be apparent from the following disclosure.

BRIEF DESCRIPTION OF THE DRAWINGS

The accompanying drawings illustrate preferred embodiments of the invention, and when taken together with the following description, serve to explain the principles and structures of the invention.

DETAILED DESCRIPTION OF THE FIGURES

FIG. 1 is an exploded perspective view of the present invention as utilized in a total hip joint prosthesis replacement procedure;

FIG. 2 is a front elevational view showing an acetabular cup in accordance with the present invention;

FIG. 3 is a side elevational view, partially broken away, to show the femoral ball cup implant and the interrelationship thereof with a femoral ball, and as procedurally positioned in a hip bone implant receiving bore;

FIG. 4 is an assembly view, partially in cross section, of the components in FIG. 1, showing a modified form thereof incorporating a plastic insert in the hip socket implant to facilitate improved interaction therebetween;

FIG. 5 is an exploded perspective view of the components constituting the hip cup implant shown in FIG. 4.

FIG. 6 is an exploded perspective view of a hip socket implant and relationship to the opening formed in the hip bone prior to insertion of the socket implant;

FIG. 7 is a front elevational view, similar to FIG. 2, of a modified form of a socket implant, and disclosing an adjusted positionment relative to the opening in the hip bone as shown in FIG. 6. This is better identified as a "Trial Cup." It can be rotated to the optimal position with notches provided for marking the bone for final insertion of the fins or blades.

FIG. 8a is a fragmentary view similar to FIG. 7, and showing the device as being secured in its adjusted position;

FIG. 8b is a view similar to FIG. 7, and showing a modified fin form 64' as a portion of the cup; and FIG. 9 is a perspective view of one of the securing fins employed in FIG. 8a, as an optional mode of fixating the cup in place.

SUMMARY OF THE INVENTION

The total hip joint prosthesis of the present invention broadly includes an acetabular cup implant adapted for placement in a prebored opening or hole in a patient's hip socket and this acetabular cup implant can be of a construction permitting its placement within the bore, and operable for an initial adjustable positioning thereof for optimum interaction with a prosthetic femoral ball or head mounted on the usual femoral prosthesis. The ball socket or opening in the implant or cup can, by rotation of an acetabular cup, define or reveal to the installing physician the optimum position of the socket to coact with the femoral ball or head regardless of the positional disposition of a patient's leg, for example. Such an acetabular cup which can be positionally rotated can be referred to as a test implant or trial implant, and such a final construction, if desired, can include the external surface porosity to facilitate intergrowth or bone structure therewith, and further the construction can provide for a plurality of positionally fixing fins mountable on the external surface of the acetabular implant following the attainment of the optimal position of the implant and ball socket. In other words, the trial cup could serve two purposes; (1) as a trial cup allowing it to be rotated into an ideal position and, (2) once so positioned, could remain in place while the fins are driven into the bone along the slotted paths (FIG. 6 and FIG. 9) ending up as in FIG. 8. The test cup can be otherwise devised for use by the implanting physician or surgeon, by rotation, and by use of indicia means on the cup or implant to permit the physician to make an installation marking adjacent the bore in the patient's hip. The test implant can then be withdrawn and replaced by an implant which includes all of the structural features including the porous exterior surface and the fixing fins, with optionally plain or porous external surfaces, and containing an indicia for matching up with the indicia adjacent the bone bore to insure appropriate placement of the acetabular cup implant in the patient.

Another and extremely important aspect of the present device resides in the configuration of the acetabular cup as a trapezoid or a portion of a truncated cone. As has been noted over a period of time, bones or bone structure in users of hip prosthesis of the type of the present invention have a certain degree or small amount of shrinkage, technically called "demineralization" or "physiological atrophy." This shrinkage has, in some prior art devices, caused a disjoinder or migration of the acetabular cup in the patient's or user's hip and there has been a tendency for separation or divorcement or painful loosening of the cup from the user's hip bone. The trapezoidal configuration of the present invention is devised to compensate for such shrinkage of the bone and maintain dynamic press positioning. It is also known that the inner surface or socket in the bone may be diseased and/or distorted from previous surgical procedures. The present device serves to exploit a bleeding inner surface, once appropriately prepared surgically, without the necessity of removing the fragile tissue while at the same time permitting the insertion of the device so that it will not rotate but will also grip the good, hard outer bone. The implant, due to its configuration, will react dynamically rather than as a static member. As bone, subsequent to placement of the implant, tends to retract or withdraw from the implant to a small degree, but nevertheless going through a shrinking action, which in the prior art caused loosening of the implant eventually had been overcome by the present device. The present design, i.e., the trapezoidal or conical shape, provides a mechanism whereby the implant structure can accommodate any such shrinking, constantly providing a dynamic and vital bony contact which aids the secondary connection and growth in the porous surface, as known in the art, into the bone for longevity of the combination in the patient's hip joint.

Hence, the physical configuration and design of the cup works constantly with bony growth around the cup to provide any necessary compensating movement, while at the same time providing the optimum initial placement and positioning fixation required for a continuing optimal intercoation of the parts and proper structural support in a firm and rigid manner. Apropos of this, the present concept or invention differs completely from the blades as shown, for example, in prior U.S. Pat. No. 3,840,904, since in the present invention, the crux of the matter is that movement can take place longitudinally of the cup, in effect translation to compensate for the bone change due to shrinkage while at the same time preventing rotation and providing a continuing secure connection. These features substantially diminish the necessity of subsequent removal of prosthesis installations from patients wherein a deterioration of bone, and/or integration between the implant and the bone has occurred. Bone movement in a physiological manner is compensated for, which keeps the bone-metal contact a healthy, continuous interdigitation between bone and implant, to provide a basis for long-range, living connection. The cone acts to provide a constant wedging of implant into bone.

Additional features and advantages of the invention will become apparent from the following.

DESCRIPTION OF THE PREFERRED EMBODIMENT

Referring now specifically to the drawings, FIG. 1 discloses in an exploded perspective view the structure contemplated by the invention and indicating usage thereof in a prosthesis of a person as a substitute or artificial replacement unit. In this figure, the pelvis of a prospective user or patient is indicated fragmentarily at 10. An acetabular cup implant is broadly indicated at 12 and is shown as being positioned in a bore or hole shown by dotted lines at 14 in the hip bone 10. As will be noted from the broken line showing of the cup at 14, the shape is trapezoidal or a portion of a cone. This is more clearly shown in other figures. The configuration of the implant 12 is more clearly shown in the fragmentary sectional view thereof in FIG. 3. FIG. 3 shows the eccentric nature of the cup, the top or superior lip being shorter than the bottom or inferior lip. This eccentricity allows a trial cup, as will be described later, to be rotated in the bony socket until the ideal position has been found as a "stable articulation" between ball and socket. Alternatively, the cup could be true with all sides being equal.

In FIG. 3, the bore 14 is also more clearly shown as being commensurate with the size and shape of the implant cup 12 and is so drilled or formed in hip bone 10 by the surgeon who is to implant the prosthesis. Referring again to FIG. 1, a femoral pin 16, as known in the art, structurally supports a femoral head or ball 18 at its upper end, and which is adapted for mating operational engagement within socket 20 in implant cup 12. It is to be noted that the external surface of the pin 16 is provided with a porous coating at 22. This porous coating is known in the art and serves the function of facilitating bone growth thereinto for permanent affixation of the member with respect to the user's bone, also as well known in the art. The material of the pin can differ, as also can the material of the femoral head 18 all as well known in the art. In one possible combination, the cup is all metal while the femoral ball may be likewise metal, but could be plastic, or a ball of ceramic articulating with a ceramic cup of this special design configuration. The material of head 18 preferably should be of a high grade plastic or metal composition to insure long lasting and non-deteriorated affixation functionally within socket 20. Head size and socket size are variable.

The inner cup or liner 14 can likewise be formed from different materials although a preferable one, as shown in FIG. 1, consists of a high grade plastic or porcelain, while the outer cup is made out of steel or steel alloys or titanium or titanium alloys. Attention is also invited to a plurality of longitudinally extended fins 24, 26 and 28. These fins will be discussed in greater detail hereinafter as regards their construction and function. Initially however, it is to be noted that these fins are positioned at spaced intervals around the outer periphery of the cup, being three as shown in the drawings. This can vary. It is also to be noted that these fins extend longitudinally of the implant cup; i.e., parallel to the axis or center line B—B of the socket 20. The fins can, as will appear hereinafter, be permanent with respect to the implant cup or can be removably mounted thereto. The external face of the fins is provided with a plurality of teeth indicated at 32, or may be plain as an option, or perforated with holes. When the implant is placed in the prepared bony bore and driven into engagement into such bore in a known manner, these fins serve the functional purpose of preventing rotation of the cup within the bore and additionally the teeth aid in preventing displacement longitudinally of the cup with respect to the bore and bone as will be readily understood, as added supplemental fixation for overall seating of the implant into the patient's socket.

Referring again to FIGS. 1 through 3 of the drawings, it is pointed out that the bore or hole 14 is drilled into the bone along a line A—A as distinguished from the center line B—B of socket 20; special cutting tools or reamers are used.

One outstanding feature of the present invention resides in the configuration of the cup implant 12. By reference particularly to FIG. 3, it will be seen that the external shape of this member 12 constitutes a portion of a truncated cone. The cup includes a front face 32 and a rear face 34. The front face 32 is not at right angles to the line or axis C—C while face 34 is at right angles to A—A, which also constitutes the longitudinal axis of the socket 20. Line B—B is perpendicular to the inner socket 20.

Referring now to FIG. 2 of the drawings, it will be seen that the socket 20 has a center on line E—E which is displaced from the center line D—D of the implant 12. This displacement is indicated by an arrow 36 in FIG. 2. The result is that the cup 20, and front face 38 thereof, are eccentric with respect to the line of rotation of the cup and longitudinal center line D—D. Rotation of the cup will cause eccentricity of movement of the socket longitudinally and through an arc. A chamfered surface 40 is provided at the opening of socket 20 for the purpose of facilitating easy insertion and movement of head or ball 18 within the socket 20.

In the showing of FIGS. 1 through 3, the fins 24 are integral with the external periphery of the implant 12 and the implant is driven into engagement as one piece within the bore or hole 14 and this position is maintained by means of the fins engaging in the material of the hip bone 10 exterior to the bore. The angular disposition of pin 16, head 18 and socket 20 are such that normal disposition or movement of a user's leg with respect to the individual members of the total hip prosthesis are as normal as possible and will cover and be operable in all normal positions of the patient's leg.

In FIG. 4, a modification of the invention is shown. The femoral ball may be preferably metal to articulate with the plastic socket. The implant cup 12A includes an outer metal, or other material, shell 44 which has mounted therein a plastic material insert 46. The plastic insert is provided with a plurality of rings 48 and 50 on the external surface for connection and mating engagement within internal rings or grooves 52, 54 in the interior surface of shell 44. The shell may be molded into permanent positioning or may be removed by a variety of standard mechanical methods. A chamfer 40A is provided in this modification and the external surface of the outer shell 44 is provided with a plurality of integrated fins of the same character and construction as fins 24-28 in FIG. 1. They serve the same function and are similarly arranged. The axes A—A; B—B; C—C; D—D and E—E in FIGS. 4 and 5 are similar to those shown in the embodiment of FIGS. 1, 2 and 3. The operation of this embodiment will accordingly be similar.

A further modification of the invention is disclosed in FIG. 6. In this embodiment, the acetabular implant cup 12B includes the same external trapezoidal configuration and includes a socket 20B eccentrically disposed in the front face 32B. In this embodiment, a plurality of grooves 58 are provided in the external surface of the implant and are longitudinally disposed. The grooves are configured as dovetailed members. An indicia mark 60 is included on the front face 32B. In effect, this embodiment of the invention can constitute a so-called dual device, a test implant unit which could be fixed into final position by fins driven along the slots or grooves in its side walls, as referred above, and can be placed within the bore or hole 14B which is similar to 14 in FIG. 1. In use the cup test unit 12B can be positionally rotatably displaced in the bore by the inserting surgeon. The eccentricity of positionment of the sockets 20, 20A and 20B will, in conjunction with the slanted front face 32, serve to rotate, together with the implant, the orientation of the sockets with respect to the bore in which inserted. It is to be noted and of substantial importance that the opening and socket will, upon rotation of the implant, have bidirectional movement, one being arcuate about the rotational axis and the opening face of the socket will be longitudinally moved slightly inward or outward due to the angular disposition of face 32.

In use of the modification shown in FIG. 6, once the surgeon has appropriately disposed the implant for optimum co-action of the ball and socket he will make a positioning indicia mark 62 in the bone surrounding the bore 14B. At that time, the test unit can be permanently fixed in place by driving fins such as seen in FIG. 9 into position.

Another possibility when utilizing the embodiment of FIG. 6 is to orient the implant in the bore and thereafter to insert in the bores 58 separate fins 64 shown in FIG. 9 and which include tapered bases 66 for connection with the dovetail configuration of grooves 58. These fins, again, are toothed at 68 similar to the teeth 29 in FIG. 3. By driving these separate fins into place in the positioned implant, the implant will be fixed. The external surfaces of the implant at 70 and the fin at 72 are porous as in the other embodiment.

The inserting manipulation and repositioning of the socket and the axis thereof for optimal intercoaction with the femoral head on the femoral pin will be more readily understood from FIGS. 7 and 8. Utilizing the embodiment of FIG. 6 as the test positioning unit, the implant 12B is positioned by the surgeon to the optimum position for co-action with the ball, the position indicator 62 being marked by reference to indicator mark 60, the axis C—C having been rotated from an initial to ultimate position through the angle indicated at 74 between arrows 76, 76 and the axis D—D being moved to the position D'—D' as shown in FIGS. 7 and 8. In this operation, the test unit 12B can either have been removed and replaced by the unit shown in FIG. 1 or FIG. 4 or the test unit of FIG. 6, after placement and rotation or orientation can have had the fins as shown in FIG. 9 driven thereinto for fixation of the implant in the bore. A modified groove configuration is shown in phantom lines in FIG. 7.

Functionally, all of the embodiments as shown will serve the same purpose of positioning the socket for optimal co-action with the ball. The socket has an orientation to the patient's pelvis in such a way that the two parts will remain stable, i.e., the ball and socket, through the entire relative movement of the implant and the ball. The orientation of the socket to the ball must be such that, or vice versa, the relative stability of the ball and socket arranged will be optimal throughout a normal range of hip motion or leg motion and the members will remain optimally functional, and the ball will not slip out of the socket.

Reemphasizing this important feature of the invention, the mouth or positionment of the cup opening in the front face of the implant is eccentrically disposed so that, when the surgeon rotates the prosthesis the mouth of the cup will orient the containment interior thereof within the implant to a stable position, covering or extending through the normal range of motion of the hip. As pointed out, this can be accomplished by a test or trial prosthesis implant with exact measurements and indicia, but omitting fins initially for the positionment.

The implant units can be of different sizes and materials and the fins can be specifically different so long as the orientation thereof is longitudinal, and they serve to grip the outer solid bone as hereinbefore described. We therefore end up with an initial fixed position of the implant and socket, the positionment is guaranteed by use of the fins and the overall configuration of the implant as a trapezoid or truncated cone will compensate for shrinkage or retraction or withdrawal of the bone, over a time period which, while only to an extremely small amount, nevertheless, shrinkage will occur. Due to this aspect of the invention, the possible loosening of the implant of the prior art is overcome and the implant can follow or conform to the shrinking over a period of time, constantly providing a bony contact which aids the secondary connection and growth of the bone into the porous surface of the implant to insure longevity of the combination.

While preferred embodiments of the invention have been shown in the drawings and described herein, manifestly minor variations therein will be obvious to those skilled in the art without departing from the spirit of the invention. Such obvious changes or modifications are considered to be within the scope of the inventive concept as expressed herein, and as claimed hereinafter.

I claim:

1. An acetabular cup for use with a femoral ball in a total hip joint prosthesis comprising:

a hollow shell having a shape of truncated cone, said cone tapering from an open face front and to a closed rear face and said shell having a central longitudinal cone axis therethrough wherein said rear face is substantially perpendicular to said cone axis and said front face subtends an acute angle with respect to the rear face; and thereby providing constant dynamic bony contact which prevents loosening of said shell in the joint; and a bearing member having an outer surface complimentary to inner surface of said shell so as to be engageable therewith when inserted through said open face; said bearing member having a socket formed therein for receiving said femoral ball, said socket defined by an axis therethrough being angularly displaced from said cone axis wherein the socket is disposed eccentrically with respect to the cone axis whereby, when the cup is rotated about its longitudinal axis, the bearing member is moved through an angular arc to permit said bearing member to be placed in an optimum position for receiving said femoral ball.

2. The cup of claim 1 in combination with means for fixing the cup in the bone to prevent rotation after the cup is rotated into its optimum position.

3. The cup of claim 2 wherein the means for fixing the cup extend longitudinally on the exterior of the truncated cone, whereby the cup can shift to accommodate any bone shrinkage.

4. The cup of claim 1, with marks thereon for indicating on the adjacent bone an optimum socket position, whereby the cup can be used as a test cup, and then replaced with a permanent cup having means thereon to prevent cup rotation.

5. The cup of claim 4 wherein the means to prevent cup rotation can be attached to the cup after the cup is inserted.

* * * * *